(12) United States Patent
Paulsen

(10) Patent No.: US 8,314,794 B2
(45) Date of Patent: Nov. 20, 2012

(54) APPARATUS AND METHOD FOR REPRESENTING A SCANNED SURFACE

(75) Inventor: Rasmus Reinhold Paulsen, Copenhagen (DK)

(73) Assignees: Oticon A/S, Smorum (DK); Widex A/S, Vaerlose (DK)

( * ) Notice: Subject to any disclaimer, the term of this patent is extended or adjusted under 35 U.S.C. 154(b) by 842 days.

(21) Appl. No.: 12/414,348

(22) Filed: Mar. 30, 2009

(65) Prior Publication Data
US 2009/0289938 A1 Nov. 26, 2009

(30) Foreign Application Priority Data
May 20, 2008 (EP) .................... 08104031

(51) Int. Cl.
*G06T 17/00* (2006.01)
(52) U.S. Cl. ...................................... 345/420
(58) Field of Classification Search .................. 345/420
See application file for complete search history.

(56) References Cited

U.S. PATENT DOCUMENTS

| 7,304,645 B2 * | 12/2007 | Blask et al. .................. 345/424 |
| 2007/0172112 A1 * | 7/2007 | Paley et al. ................... 382/154 |
| 2008/0238919 A1 * | 10/2008 | Pack .............................. 345/420 |

FOREIGN PATENT DOCUMENTS
WO    WO-2005/008283 A1    1/2005

OTHER PUBLICATIONS

Ohtake et al., "Multi-level Partition of Unity Implicits", ACM Transactions on Graphics USA, vol. 22, No. 3, Jul. 2003, pp. 463-470, XP002501904, ISSN: 0730-0301.

Chen et al., "Generalized MPU Implicits Using Belief Propagation", 3D Digital Imaging and Modeling, 2007, (3DIM 2007), Sixth International Conference on IEEE, Piscataway, NJ, USA, pp. 400-407, XP031131022, ISBN: 978-0-7695-2939-4, Aug. 2007.

Hoppe et al., "Surface Reconstruction from Unorganized Points", Computer Graphics, ACM, US, vol. 26, No. 2, Jul. 1, 1992, pp. 71-78, XP000972231, ISSN:0097-8930.

Bernardini et al., "The Ball Pivoting Algorithm for Surface Reconstruction", IEEE Transactions on Visaualization and Computer Graphics, IEEE Service Center, Los Alamitos, CA, US, vol. 5, No. 4, Oct. 1, 1999, pp. 349-358, XP0000908551, ISSN: 1077-2626.

Klein et al., "Point cloud surfaces using geometric proximity graphs", Computers and Graphics, Elsevier, GB, vol. 28, No. 6, Dec. 1, 2004, pp. 839-850, XP004615301, ISSN: 0097-8493.

* cited by examiner

*Primary Examiner* — Edward Martello
(74) *Attorney, Agent, or Firm* — Birch, Stewart, Kolasch & Birch, LLP

(57) ABSTRACT

Disclosed is a method for generating a digital representation of a surface of an object from point data indicative of coordinates of points on the surface. The method comprises receiving a point data item indicative of coordinates of a point in a first one of a plurality of sub-volumes of a volume to be scanned; determining whether a first predetermined trigger condition is fulfilled for the first sub-volume; and if the first trigger condition is fulfilled, computing a local surface representation associated with the first sub-volume from received point data items associated with at least the first sub-volume; determining whether a second predetermined trigger condition is fulfilled; and if the second trigger condition is fulfilled, computing a surface representation of the surface of the object from a set of computed local surface representations associated with respective sub-volumes.

19 Claims, 6 Drawing Sheets

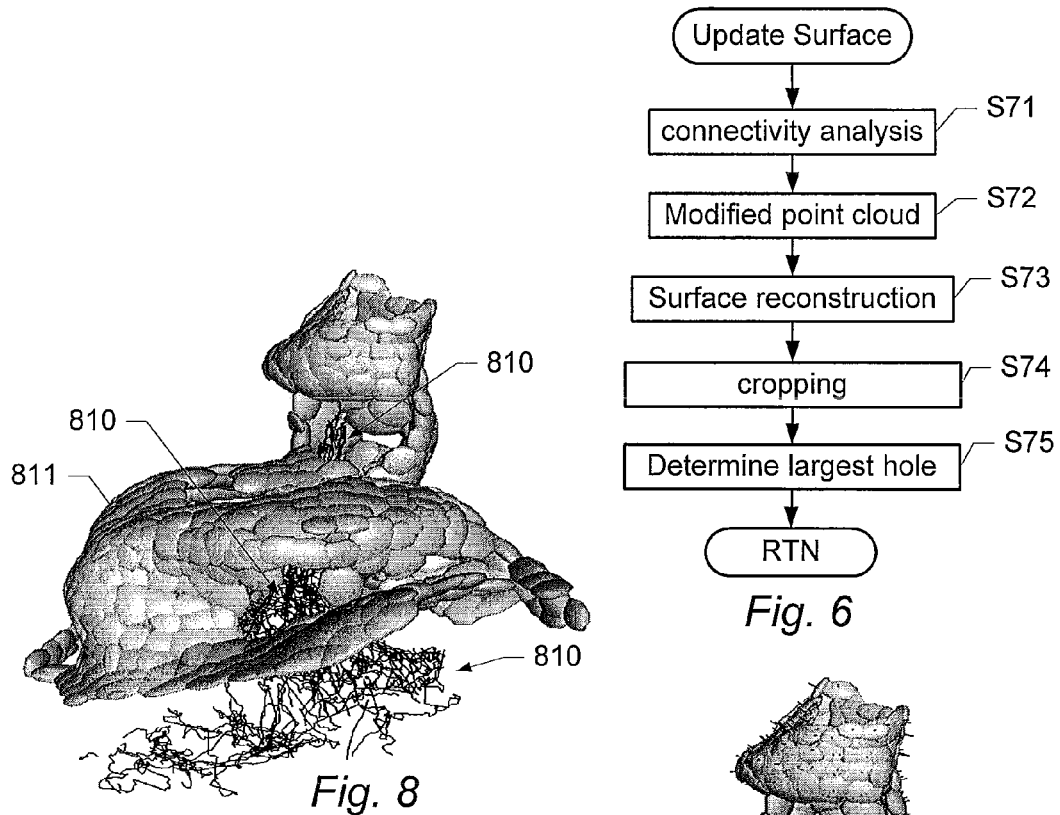
Fig. 6
Fig. 8
Fig. 9
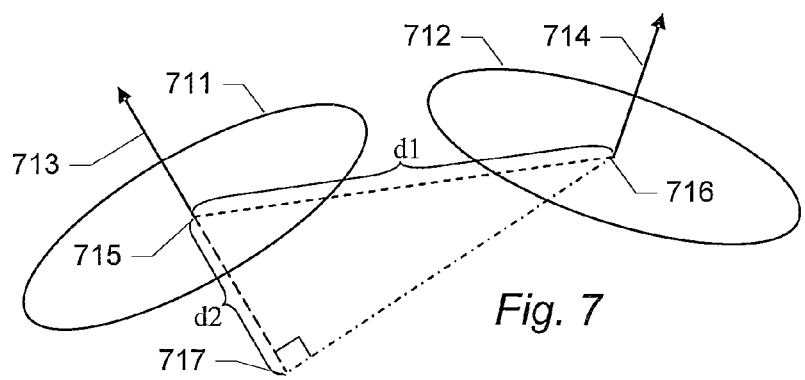
Fig. 7

APPARATUS AND METHOD FOR REPRESENTING A SCANNED SURFACE

TECHNICAL FIELD

The present invention is related to a method and an apparatus for generating a digital representation of a scanned surface from geometrical data obtained by a scanning process of the surface, e.g. the internal surface of a cavity such as the ear and ear canal of the human body.

BACKGROUND

Range scanners as for example laser scanners may be used to generate a digital representation of a surface of an object. Typically, range scanners generate an output indicative of 3D coordinates of each of a plurality of points. The result of scanning an object is therefore a collection of points, also called a point cloud.

An interesting application of such a method and apparatus includes the generation of a data mapping of the internal surface of the ear and ear canal, so that 3-dimensional data or a digital model of the internal surface of the ear and ear canal can be obtained. Such a 3-dimensional model can be used to produce a shell, which has the exact shape of the canal and the shell may form the basis for an In-The-Ear (ITE) or Completely-In-The-Canal (CIC) hearing aid. Also ear moulds or shells for other purposes such as a hearing protection or for headsets may be produced from the data model. The shell can be produced on the basis of the data model in different ways, such as by recent developed rapid prototyping methods or by well known machining, e.g. in a Computer Numerically Controlled (CNC) machining centre.

The advantage of having a data model of the ear canal, e.g. compared to traditional manufacturing processes based on ear impressions taken by introducing a semi-fluent, curable material into the ear canal, is that the production of the shell can take place at any location. This in turn allows a centralisation of the shell production at a central production facility, thereby facilitating the maintenance of a uniform quality. Further so the data model may be transmitted either as it is obtained or right thereafter for evaluation at a production facility. Thereby a data model of the hearing aid may be generated, which may be realized based on the dimensions and shape of the canal. The data model of the hearing aid can be transmitted back to the end user for visual evaluation.

International patent application WO 02/091920 discloses a method and apparatus for obtaining geometrical data relating to the internal surface of the ear and ear canal of the human body in order to be able to generate a model of the internal surface of the ear and ear canal. To this end this prior art document discloses a probe having a longitudinal axis, where light is emitted from a mirror at the tip of the probe in a right angle away from the longitudinal axis of the probe and towards the surrounding canal wall. The apparatus comprises a detector for detecting reflected light from the canal wall, and analysing means for determining the distance from the probe to the internal surface of the canal at points of the circumference.

The point cloud data resulting from the scanning process of a surface of an object may be further processed on a data processing system so as to generate another digital representation of the surface, such as a triangulated surface. This process is called surface reconstruction.

Hence, once the entire surface of an object has been scanned by means of a scanner, a surface reconstruction process may be performed on a computer allowing a reconstructed surface to be displayed and saved. However, in certain circumstances the scanner is operated by a user during the scanning, e.g. when using a hand-held scanner that is constructed as a combined ranger scanner and 3D position system, or a scanner with a handheld probe, In such situations, it is desirable that the user operating the scanner receives some kind of feedback during scanning so as to allow the user to determine whether sufficient data has been obtained and/or whether all parts of the surface have been sufficiently covered by the scanning process. In particular, it would generally be desirable for the user to be able to see a 3D model of the surface already scanned. Unfortunately, due to the massive amount of computation required for surface reconstruction, it is very difficult to generate surface reconstructions during scanning, i.e. in real-time or near real-time.

SUMMARY

According to one aspect, disclosed herein is a method for generating a digital representation of a surface of an object from point data indicative of coordinates of points on the surface. Embodiments of the method comprise:

a) receiving a point data item indicative of coordinates of a point in a first one of a plurality of sub-volumes of a volume to be scanned;

b) determining whether a first predetermined trigger condition is fulfilled for the first sub-volume; and if the first trigger condition is fulfilled, computing a local surface representation associated with the first sub-volume from received point data items associated with at least the first sub-volume;

c) determining whether a second predetermined trigger condition is fulfilled; and if the second trigger condition is fulfilled, computing a surface representation of the surface of the object from a set of computed local surface representations associated with respective sub-volumes.

Hence, embodiments of the method described herein use an iterative update method. For every point added to the point cloud, a small and local computation is done. When the surface visualisation is refreshed, only the results of the small and local computations are considered, thus eliminating the need of considering the full point cloud for each refresh. Hence, some embodiments of the method described herein use a combination of 3D spatial caching, local computations, and fast iso-surfacing. The inventors have found that embodiments of the method described herein allow generation of accurate 3D surface reconstruction in near real time.

In some embodiments, the method comprises measuring coordinates of points on the surface of the object so as to generate a sequence of point data items indicative of coordinates of the respective points, and performing above steps a) through c) for each of the generated point data items. The measuring and the surface generation including steps a) through c) may be performed as concurrent processes, thereby allowing displaying of updated digital representations on a display during the measuring process.

The point data items may be obtained by any suitable measuring technique, e.g. by a range scanner such as a laser scanner. When scanning a surface of an object so as to obtain a digital representation of the surface, the location of the scanner in relation to the object is normally also determined and stored together with the measured point data. Based on the scanner location and a measured point location, an estimate of the local normal of the surface can be computed.

The local surface representation may be computed using any suitable method. In some embodiments, the point cloud is locally approximated by ellipsoids. The ellipsoids may be calculated from the eigenvectors and/or covariance structure calculated from respective parts of the point cloud using a Principal Component Analysis.

It is noted that features of the methods described above and in the following may be implemented at least in part in software or firmware and carried out on a data processing device or other processing means caused by the execution of program code means such as computer-executable instructions. Here and in the following, the term processing means comprises any circuit and/or device suitably adapted to perform the above functions. In particular, the above term comprises general- or special-purpose programmable microprocessors, Digital Signal Processors (DSP), Application Specific Integrated Circuits (ASIC), Programmable Logic Arrays (PLA), Field Programmable Gate Arrays (FPGA), special purpose electronic circuits, a data processing system such as a computer, e.g. a personal computer, etc., or a combination thereof.

The present invention relates to different aspects including the method described above and in the following, and corresponding systems, devices, and/or product means, each yielding one or more of the benefits and advantages described in connection with the first mentioned aspect, and each having one or more embodiments corresponding to the embodiments described in connection with the first mentioned aspect and/or disclosed in the appended claims.

In particular, embodiments of an apparatus for obtaining geometrical data relating to a surface of an object comprise:
- a measurement unit for obtaining point data items indicative of coordinates of respective points on the surface; and
- a processing unit configured to perform the method defined above and in the following.

Embodiments of the apparatus described herein may use electromagnetic radiation such as light to determine the distance from a probe to the surface. Based on a determined position of the probe, this information may be used to generate information about the shape of the surface. In some embodiments, e.g. when the surface is a surface of human skin, e.g. in the case of a human body cavity such as an ear canal, it may be advantageous to use light in the wavelength range of approximately 400-600 nm, even though electromagnetic radiation in other wavelength ranges may be suitable, e.g. visible light, infra-red light, ultra-violet light, or other parts of the electromagnetic spectrum. Different wavelength ranges may be suitable depending on the material of the surface.

During use of the apparatus, the surface need not be touched during measurement, and this is advantageous for at least two reasons. Firstly, the surface may be very sensitive, as is e.g. the case for the ear canal, such that touching thereof may be unpleasant for the subject. Secondly, the surface may deform when touched, and this might disturb the measured distance values and thereby corrupt the obtained data model.

The apparatus may comprise a probe having an end portion, radiation directing means for directing electromagnetic radiation from probe to at least one location on the surface so as to cause the radiation to be reflected from said location, detection means for detecting the reflected radiation from the at least one location, and means for determining from the detected radiation a distance between the probe and the surface. The radiation detecting means may comprise an array of light sensitive elements such as CCD elements, thereby providing a location-sensitive detection of the reflected light.

In one embodiment, position data about a position of the probe with respect to a reference system are obtained using transducing means transmitting a magnetic field associated with the probe and second transducing means fixed relative to the object, and detecting the magnetic field generated by the transmitter. The use of this method of obtaining the position data is very precise. Further it is possible to make the measurement noise insensitive. Also the transmitter of the magnetic field may be made small, so that it may easily be build into the tip of the probe.

BRIEF DESCRIPTION OF THE DRAWINGS

FIG. 6 shows a flow diagram of an example of the surface reconstruction step of the method of FIG. 2.

FIG. 7 illustrates an example of a measure of connectedness between local surface representations.

FIG. 8 shows the local surface representations of FIG. 5 and the scanner path of the scanner that has obtained the point cloud.

FIG. 9 shows the local surface representations of FIG. 5 and their respective local surface normals.

Throughout the drawings, equal reference signs refer to equal or corresponding elements, features, or components.

DETAILED DESCRIPTION

Figure 1:
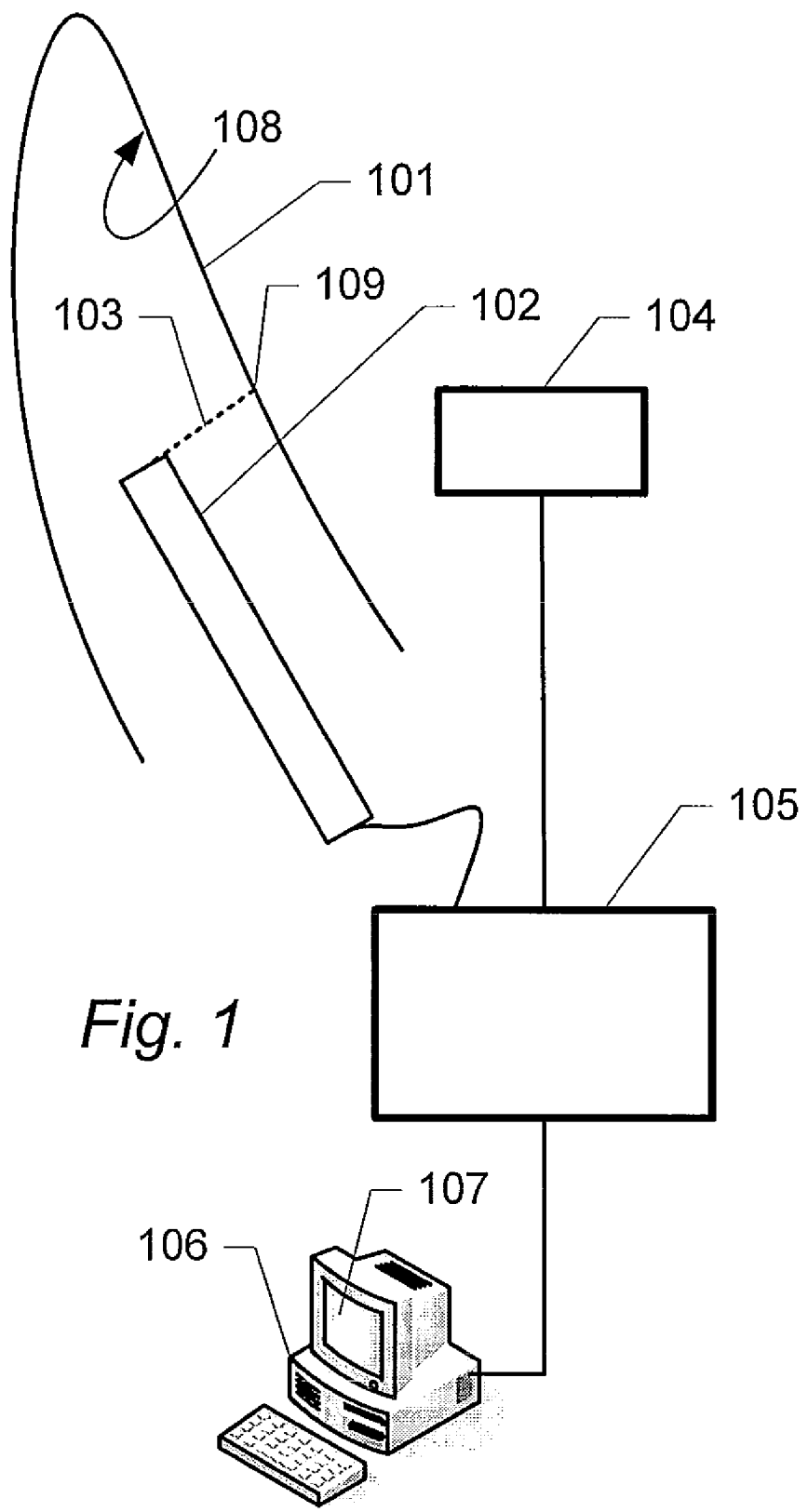
FIG. 1 shows a schematic view of an example of an apparatus for obtaining geometrical data relating to the internal surface of a cavity and for generating a digital representation of the surface.

FIG. 1 shows a schematic view of an example of an apparatus for obtaining geometrical data relating to the internal surface 108 of a cavity 101 and for generating a digital representation of the surface 108.

The apparatus comprises a sensor probe 102 for insertion into the cavity 101 and for measuring the distance 103 from the probe 102 to a point 109 on the surface 108. The probe 102 may utilise any suitable method for measuring the distance/range, e.g. an optical range scanner based on electromagnetic radiation such as light. An example of such a probe is disclosed in WO 02/091920 incorporated herein by reference in its entirety. For the purpose of the present description, the probe will also be referred to as scanner. The probe is connected to a signal processing unit 105 for processing received signals from the probe 102. The signal processing unit 105 is further connected and receives signals from a sensor unit 104 configured to determine the position of the probe 102 relative to the surface 108. For example, the determination of the position of the probe may be based on a magnetic field generated by one or more coils included in the probe 102, e.g. as disclosed in WO 02/091920. From the signals received from the probe 102 and the signals received from the sensor unit 104, the signal processing unit 105 computes coordinates of the point 109 relative to a suitable coordinate system, e.g. a Cartesian coordinate system. An operator may move the probe 102 around inside the cavity 101 and measure coordinates of a plurality of points so as to obtain a point cloud of a plurality of points indicative of the surface 108. The signal processing unit 105 forwards the thus obtained point coordinates to a data processing system 106, e.g. a suitably programmed computer. For example, the data may be forwarded via a suitable wired or wireless communications interface, e.g. a serial or parallel interface, a computer network, or by any other suitable data connection. In some embodiments, the signal processing unit 105 and the data processing system 106 may even be integrated into a single signal and data processing apparatus. The data processing system 106 may store the received point coordinates and/or output the data for use by another data processing system and/or display them as a point cloud on a display 107. The data processing system may further process the received point cloud data, e.g. for reconstructing the surface resulting in a digital representation of the surface. The signal processing unit 105 may further forward the location of the scanner in relation to the object together with the point cloud data to the data processing system where it may be stored and used in the further processing. For example, the coordinates of each point of the point cloud may be forwarded and stored associated with a corresponding position of the scanner.

Hence, in relation to FIG. 1, an example of an apparatus for obtaining geometrical data has been described. It will be appreciated, however, that the method described herein may be applied to different types of scanning apparatus, e.g. range scanners such as laser scanners. Other examples of such apparatus include the scanning apparatus marketed under the name Fastscan by Polhemus, Colchester, Vt., USA.

During the scanning process, the data processing system 106 generates an approximate digital representation of the surface 108 in real time or quasi/near real time based on the point data received so far, and displays the approximate digital representation on the display 107. Hence, an operator receives feedback about which portions of the surface are already covered by sufficient points and which surfaces still require further scanning. The data processing system may even determine surface parts that require further scanning and indicate these parts on the display. Alternatively or additionally, the data processing system may provide other visual aids for guiding the operator during the scanning process. An embodiment of a process for incremental generation of such an approximate representation will be described below.

Figure 2:
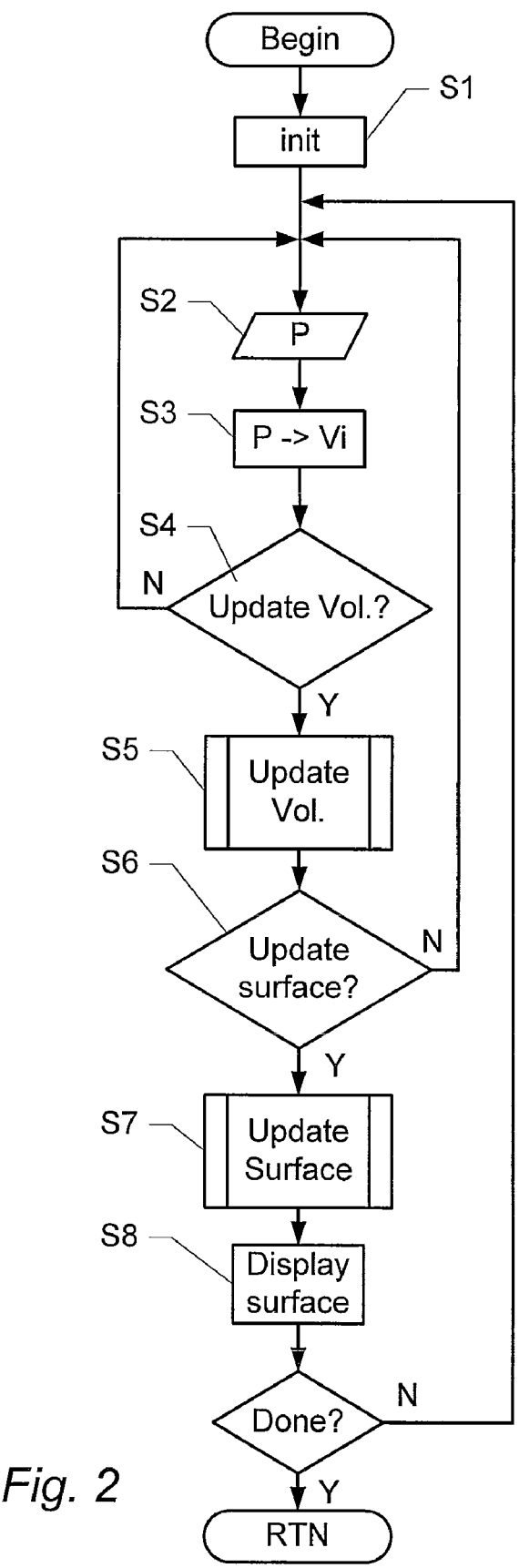
FIG. 2 shows a flow diagram of an example of a method for incremental generation of an approximate digital representation of a surface.

FIG. 2 shows a flow diagram of an example of a method for incremental generation of an approximate digital representation of a surface.

Figure 3:
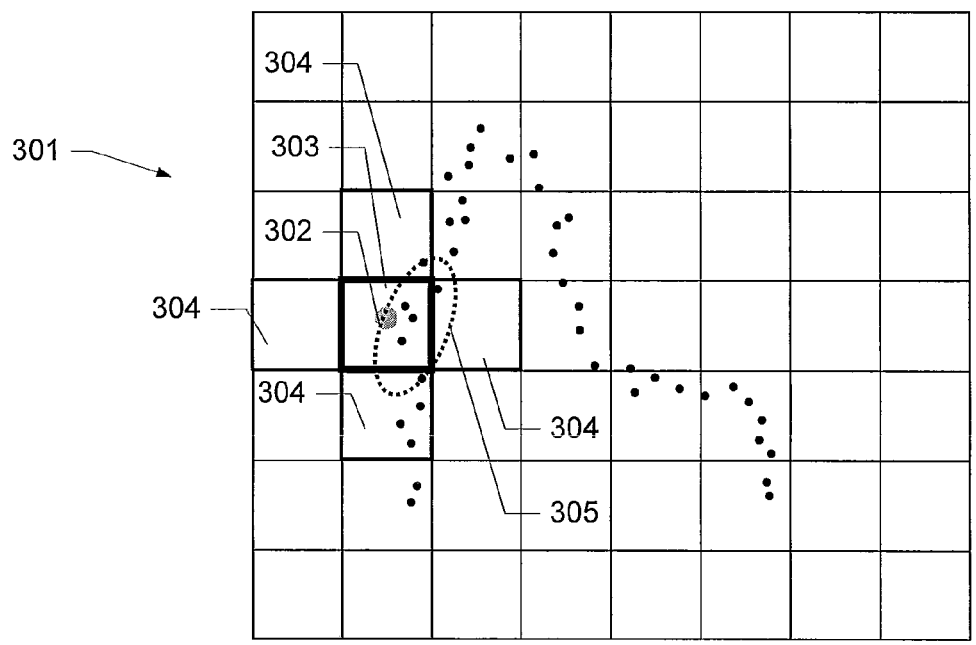
FIG. 3 schematically illustrates a sectional view of a scan volume.

The process starts at step S1 where the process is initialised. In particular, the process divides a 3D volume to be scanned into a set of sub-volumes, preferably non-overlapping sub-volumes. The sub-volumes may have any suitable size and form, e.g. cubes, rectangular boxes, cylinder segments, etc. In the following the sub-volumes will also be referred to as volume cells or simply cells. When their geometry is matched to the coordinate system used to represent the volume to be scanned, the subsequent process is particularly effective. FIG. 3 schematically illustrates a sectional view of a cubic volume 301, i.e. the section of the volume 301 is shown as a square. The volume 301 is divided into equal sized cubic cells. One of the cells is designated by reference numeral 303. A number of received points are illustrated as black dots. During the initialisation step 301, the process may initialise further data structures, e.g. data structures assisting efficient identification and/or indexing of the generated sub-volumes, e.g. a look-up table indicating for each sub-volume a number of neighbouring sub-volumes defining a respective predetermined proximity/neighbourhood for each sub-volume. For example, cells 304 define a neighbourhood of cells 303. However, it will be appreciated that neighbourhoods of different size and geometry may be defined, e.g. neighbourhoods including a different number of cells.

Figure 4:
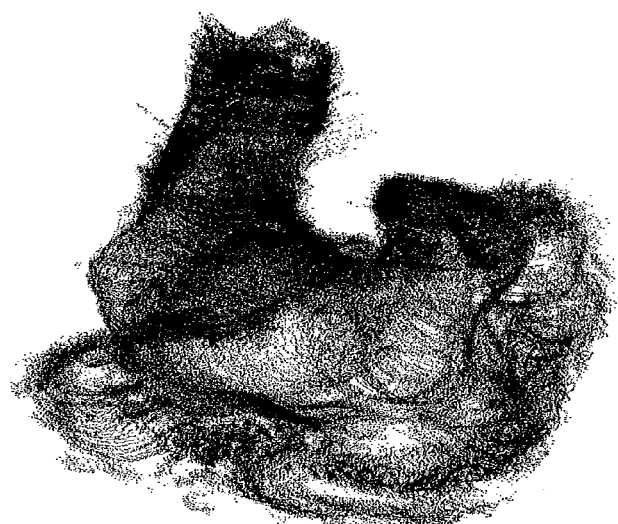
FIG. 4 shows a point cloud of an internal surface of a cavity.

The process continues at step S2 where the process receives coordinates of a point on the surface to be reconstructed. For example, the process may receive a stream of points, e.g. from a scanning apparatus as described above during a scanning process. For example, the process may receive the point data as x,y,z-coordinates in a Cartesian coordinate system. For the purpose of the present description, it will be assumed that the following steps are performed for each received point. However, it will be appreciated that the process may also be performed by receiving and buffering a number of points and then processing the buffered points while subsequent points are received and buffered. In FIG. 3, the most recently received point is designated by reference numeral 302. FIG. 4 shows a point cloud of an internal surface of a cavity. The point cloud has a varying density of points resulting in some portions of the surface to only be sparsely covered by points.

In subsequent step S3, the process identifies which of the sub-volumes the received point lies in, and the process assigns the received point to the identified sub-volume. The identification of a sub-volume may be implemented very efficiently. For example, when the geometry of the sub-volumes matches the coordinate system used, the sub-volume may be identified by simple integer division of the point coordinates. For example, the process may maintain a data structure, e.g. a list, for each sub-volume indicative of the point coordinates of the points associated with that sub-volume. In the example of FIG. 3, the received point 302 is assigned to cell 303. In the following, the cell 302 to which the received point 303 is assigned will also be referred to as the "current cell."

In subsequent step S4, the process determines how many points the current cell 303 includes. If the number exceeds a predetermined threshold, the process proceeds at step S5 and computes a local surface representation 305 of the scanned surface associated with the current cell 303; otherwise, the process returns to step S2 and receives the next point. The threshold number may be any suitable number of points, e.g. 100 points. It will be appreciated that the process may use alternative or additional trigger conditions to determine whether to proceed at step S5 or whether to receive one or more additional points. For example, the trigger condition may be based on the number of points included in the current cell 303 and the number of points included in the cells 304 of the neighbourhood of the current cell 303. Alternatively or additionally, when a local surface representation associated to the current cell has already been computed during a previous iteration of the process, the process may determine how many points have been added to the current cell, since the local surface representation associated with the current cell 303 was calculated. For example, the process may proceed at step S5 only if the number of points added to the current cell since the previous computation of a local surface representation associated with the current cell exceeds a predetermined threshold. It will also be appreciated that the threshold(s) used in the trigger condition may be selected to be any suitable number, e.g. a number that may be selected by the operator, e.g. in a configuration menu or dialog box, thereby allowing the user to adjust the frequency of updating the local surface representation to the available computational resources of the data processing system on which the process is executed.

In subsequent step S5, the process computes a local surface representation 305 approximating the scanned surface in a predetermined proximity of the current cell 303. In particular, the process may compute a local surface representation from the points assigned to the current cell 303 and from the points of the predetermined neighbourhood of neighbouring cells 304. The process may use a lookup table determine the neighbour cells that are included as described above. The number of neighbour cells that are included may be a predetermined or user-selectable parameter. The more neighbours the smoother and less detailed the final surface will be.

In one embodiment of the process, the surface reconstruction is based on the fact that a point cloud can be approximated locally using ellipsoids. This can be seen in FIG. 5 where the point cloud of FIG. 4 is approximated by a number of fitted ellipsoids. In the example of FIG. 3, an ellipsoid 305 calculated for current cell 303 is shown. Each ellipsoid may be computed using a principal component analysis (PCA) of the points in the near surrounding, e.g. in the predetermined proximity defined by the neighbour cells. The shape of the ellipsoid may be used to determine whether a part of the sampled surface is actually present or if the points in this local region are just noise. The ellipsoid should ideally be flat. A local plane-likelihood may be expressed as the percent of the variation explained by the two first Eigenvectors computed by the PCA, while the magnitude of the third Eigenvector is proportional to the local noise. In one embodiment, the process generates an ellipsoid (or updates a previously computed ellipsoid) only if the two first Eigenvectors explain a minimum threshold fraction of the variation. The threshold may be selected depending on the available computational resources and the scanning equipment used. Examples of suitable thresholds include thresholds in the range of 85%-90% of the variation. The local surface representation may be calculated from the covariance structure of the local point cloud, e.g. the point cloud of the current cell and a predetermined neighbourhood of cells around the current cells. It may be computed as an ellipsoid by stretching a sphere in the directions of the Eigenvectors. The position of the (center of the) ellipsoid is computed as the average of the (x,y,z)-coordinates of the points used in the local PCA. A local surface normal may thus be defined as a unit vector in the direction of the third Eigenvector from the centre of the ellipsoid. However, the normal of different ellipsoids may not necessarily all have the same orientation, as they may either point "into" the scanned object or out of the object. Initially, the orientation of the local surface normal may be defined relative to the scanner path of the scanner/probe that has obtained the point cloud data. To this end, the process determines the closest position on the scanner path from the current ellipsoid, and defines the local surface normal so as to point away from the path. FIG. 8 shows a number of local surface representations 811 and the scanner path 810. The scanner path may be recorded by any suitable detection mechanism, e.g. by the sensor unit 104 shown in FIG. 1, e.g. as a sequence of coordinates. FIG. 9 shows a number of local surface representations and their respective local surface normals. Due to noise and other factors, the thus determined directions of the local surface normals may not always be consistent. A voting scheme that correctly orients the normals is applied in a later step as explained in detail later. Example of a process of approximating surface patches using PCA are described in H. Hoppe: "Surface reconstruction from unorganized points", PhD Thesis, Dept. of Computer Science and Engineering, University of Washington, June 1994, and in J. C. Carr, R. K. Beatson, J. B. Cherrie T. J. Mitchell, W. R. Fright, B. C. McCallum and T. R. Evans: "Reconstruction and Representation of 3D Objects with Radial Basis Functions", ACM SIGGRAPH 2001, Los Angeles, Calif., pp. 67-76, 12-17 Aug. 2001.

Figure 5:
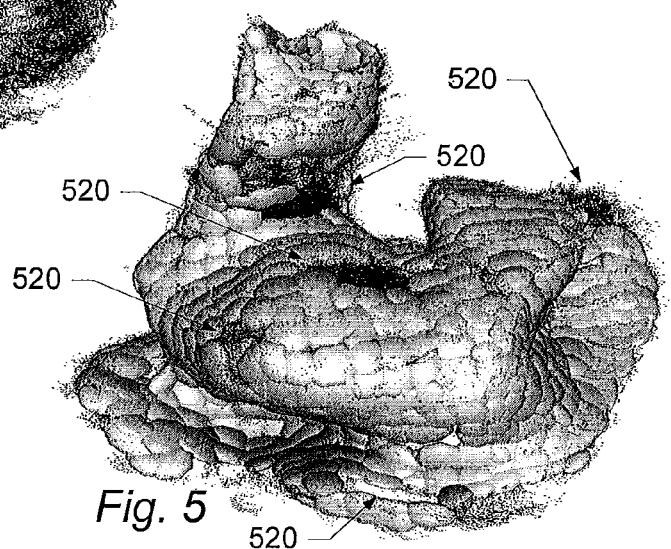
FIG. 5 shows the point cloud of FIG. 4 and local surface representations in the form of ellipsoids fitted to the point cloud.

The process stores the computed local surface representation 305 in a suitable data structure associated to the current cell 303. Hence, after each pass through step S5 each cell has associated with it either none or one local surface representation. FIG. 5 shows an example where some parts of the surface are covered by local surface representation in form of ellipsoids, while some other parts are not yet covered by local surface representations, e.g. the surface portions designated by reference numerals 520. The process keeps track of the number of cells for which a local surface representation has been calculated or updated, e.g. by incrementing a counter each time a local surface representation is calculated/updated.

In subsequent step S6, the process determines whether the number of calculated/updated local surface representations is larger than a predetermined threshold. Again, the threshold may be a pre-set and/or a user-selectable parameter. For example, the threshold may be set to 100. If the number of calculated/updated local surface representations is larger than the predetermined threshold, the process proceeds to step S7 and performs a surface reconstruction of the entire surface; otherwise the process returns to step S2 and receives a new point.

In step S7, the process performs a surface reconstruction of the entire surface, i.e. for the entire scan volume 301, based on the local surface representations calculated so far. In one embodiment, the surface reconstruction of step S7 is performed by performing a connectivity analysis of the calculated local surface representations, a surface reconstruction step, and a surface cropping step, as will be described in greater detail below.

Figure 14:
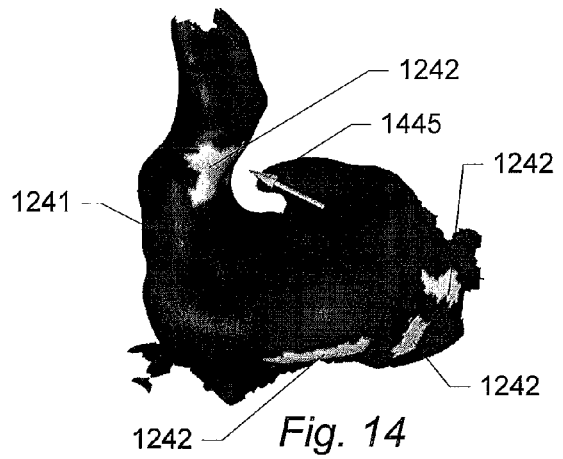
FIG. 14 shows an example of a reconstructed surface.

In step S8, the reconstructed surface is displayed to the user, and the process returns to step S2, unless the process is terminated, e.g. responsive to a user input. The display of the reconstructed surface may include the surface and optionally additional information. For example, as shown in FIG. 14, an indication of surface parts not yet sufficiently supported by the scanned points and/or an indication of the largest unsupported area may be shown.

FIG. 6 shows a flow diagram of an example of the surface reconstruction step S7, while FIG. 10 illustrates different sub-steps of an example of the surface reconstruction step. The surface reconstruction step receives the local surface representations as an input, i.e. in one embodiment the local ellipsoids. In an initial step S71, the process performs a connectivity analysis so as to remove outliers. To this end, the process groups the local surface representations into connected clusters, e.g. by means of a flood-fill type graph algorithm.

The process may determine two neighbouring local surface representations as being connected based on a suitable criterion for connectedness, e.g. a criterion based on the distance between the local surface representations and their relative orientation. FIG. 7 illustrates an example of a measure of connectedness between local surface representations. The distance between local surface representations 711 and 712 may be defined as the distance d1 between their respective centres of mass 715 and 716. The relative orientation of the local surface representations may be determined as the angle between their respective surface normal 713 and 714. The angle is taken as an absolute value (or modulo 90°) since the orientation of the surface normal are arbitrary. For example, one normal may point "into the shape" and the other "out of the shape". The maximum allowed distance between two local surface representations and the maximum angle may be pre-set and/or user-selectable parameters. In one embodiment, the maximum allowed distance is a user-selectable parameter, as it depends on the data. For surface reconstructions of the human ear canal, maximum distances of between 1 mm and 3 mm have been found useful. Similarly, a threshold for the angle of e.g. 30° has been found suitable.

It will be appreciated that additional or alternative measures of connectedness may be applied. For example, in some embodiments, a second distance d2 is used in addition to the distance d1 and the angle between normal. The distance d2 is the distance of the projection 717 of the centre 716 of one of the neighbouring local surface representations 712 onto the direction of the local surface normal 713 of the other local surface representation 711 from the centre 715 of the other local surface representation 711. This distance d2 may also be referred to as the projected distance. By requiring that the projected distance is smaller than a predetermined maximum distance, it may be ensured that two neighbouring local surface representations are placed approximately on the same plane. Again the maximum allowable projected distance is a pre-set and/or user-selectable parameter. For surface reconstructions of the human ear canal, a maximum projected distance of 1 mm has been found useful.

Figure 10A:
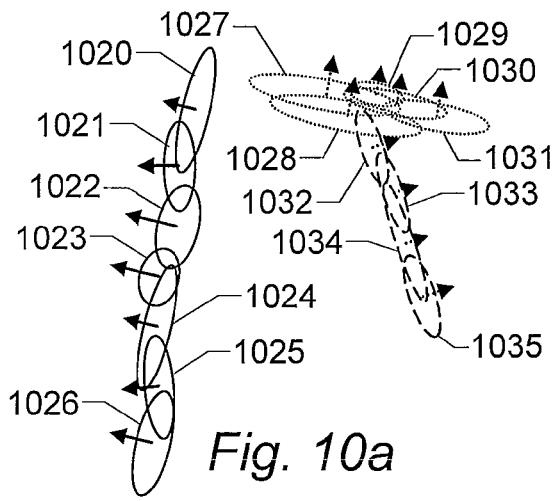
FIG. 10 illustrates different sub-steps of an example of the surface reconstruction step.

FIG. 10a illustrates an example of the flood fill algorithm. FIG. 10a shows a number of local surface representations 1020-1035 including their respective local surface normal. The flood-fill algorithm may initially select an arbitrary local surface representation, and then determine which other local surface representations the selected local surface representation is connected to based on the above criteria. This may be done by comparing the selected local surface representation with all other local surface representations. Alternatively, a faster embodiment may determine the neighbours of the cell to which the selected local surface representation is associated, and only search for potential neighbour local surface representations in the thus determined neighbour cells. The neighbour cells of a selected cell may be efficiently identified by means of a fixed lookup table that for each cell includes indices of the corresponding neighbour cells. The process may mark all neighbours of the selected local surface representation that are determined to be connected (e.g. based on the above measure for connectedness) to the selected local surface representation as belonging to the same cluster as the selected local surface representation. Subsequently the neighbour local surface representations of all the local surface representations found in the previous steps are located. This process is repeated until no new cluster members are found. The remaining local surface representations that are not marked in the previous marking round are now used in a new marking round. This is repeated until all local surface representations have been marked. At the end of this flood-fill process all local surface representations belong to a cluster, where some clusters may consist of only a single local surface representation. In the example of FIG. 10a, the local surface representations belonging to respective clusters are indicated by different line stiles: One cluster includes local surface representations 1020-1026, a second cluster includes local surface representations 1027-1032, while a third cluster includes local surface representations 1032-1035.

The process may proceed with all clusters that have a predetermined minimum number of members. The minimum number of members may be a pre-set and/or user-selectable parameter. For surface reconstructions of the human ear canal, a minimum number of 5 has been found useful.

As mentioned above, the third Eigenvector corresponds to the local surface normal of a local surface representation. However, these normals may not necessarily all have the same orientation, as they may either point "into" the scanned object or out of the object. To ensure consistent normal directions the process assigns consistent orientations to the local surface normals of all local surface representations of each cluster, e.g. by using a voting scheme. The voting scheme may be a two-step process: Initially, all normal directions are forced to be consistent by the above-mentioned flood-fill algorithm. When a new cluster member is marked, its surface normal is compared to the normal of the cluster member that initially "caught" it during the marking process. If the angle between their surface normals is greater than 90 degrees, the normal of the new cluster member is flipped. In a second step, the normal of each local surface representation is compared to the scanner path as described above, and the process counts how many normals point into the object (i.e. towards the scanner path) and how many point outward (i.e. away from the scanner path). If a majority of normals point inward, the process flips all normals so as to point inward, and vice versa. An example of such a voting scheme is also described in H. Hoppe (ibid.).

Still referring to FIG. 7, in subsequent steps S72-S73, the process performs surface reconstruction using a so-called implicit method for surface reconstruction, e.g. by use of a commercially available toolkit such as the FastRBF toolkit marketed by FarField Technology Limited, Christchurch, New Zealand, or any other tool that uses implicit methods to do surface reconstruction.

In the following, a short introduction to implicit methods is given: In an implicit method the goal is to generate a function f(x,y,z) that implicitly defines the sought surface. FastRBF is based on a set of functions called Radial Basis Functions (RBFs); for a more detailed description of RBFs, reference is made to J. C. Carr, R. K. Beatson, J. B. Cherrie T. J. Mitchell, W. R. Fright, B. C. McCallum and T. R. Evans: "Reconstruction and Representation of 3D Objects with Radial Basis Functions". ACM SIGGRAPH 2001, Los Angeles, Calif., pp. 67-76, 12-17 Aug. 2001. However, other basis functions can also be used, see e.g. M. Kazhdan, M. Bolitho, H. Hoppe: "Poisson surface reconstruction". Symposium on Geometry Processing 2006, 61-70. For the purpose of the present description, it may suffice to note that a 3D function f(x,y,z) can be constructed that fits the input data in such a way that f(x,y,z)=0 for all sample points and f(x,y,z)!=0 every else. A triangulated surface is then found by using a standard isosurface extractor on f(x,y,z), e.g. meaning that the surface follows the function f where it is equal to zero. The marching cubes algorithm is described in William E. Lorensen, Harvey E. Cline: Marching Cubes: A high resolution 3D surface construction algorithm. In: Computer Graphics, Vol. 21, Nr. 4, July 1987. It is also mentioned on page 20 line 12. An alternative algorithm is described in Bloomenthal, J. An Implicit Surface Polygonizer, Graphics Gems IV (P. Heckbert, ed.), Academic Press, New York, 1994. In embodiments of the present method, the function f(x,y,z) is fit to a modified point cloud by generating artificial off-surface points, i.e. points different from the obtained points and located at e.g. predetermined distances from the local surface representations. The collection of offset points is called a density representation.

Accordingly, in step S72 the process generates a modified point cloud from the local surface representations by generating a density representation comprising artificial off-surface points. In particular, the density may be computed by creating two points for each local surface representation: one with a value of −1 in the opposite direction of the local surface normal associated with the local surface representation, and one with a value of +1 in the direction of the normal.

In subsequent step S73, the process reconstructs a surface from the modified point cloud, e.g. by use of FastRBF or another suitable toolkit for using an implicit method for surface reconstruction. The process may determine a function f(x,y,z) from the modified point cloud that implicitly defines an approximation of the surface. Furthermore, the original centre of the ellipsoid is not used. When f(x,y,z) is fitted to these points, f(x,y,z)=1 at the outside of the shape and f(x,y,z)=−1 in the inside. This is why the method is called implicit, since the iso-surface where f(x,y,z)=0 is implicitly defined using the off-surface points. The surface is the generated by an iso-surface extracting process. Iso-extraction is a technique well-known in the art as such. One example of a method for iso-extraction is the so-called marching cubes method, while FastRBF uses another method.

Figure 10B:
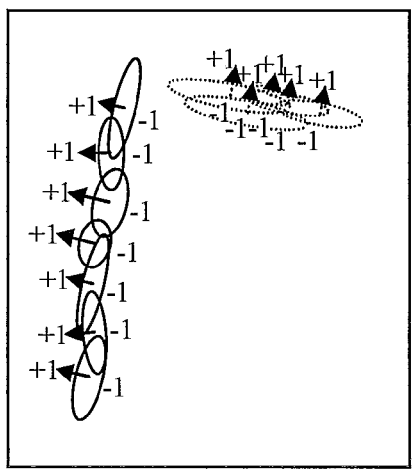
Figure 10C:
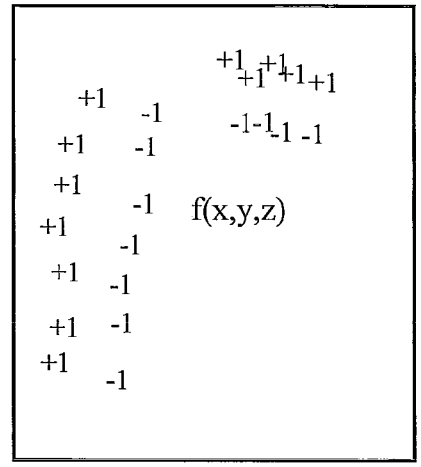
Figure 10D:
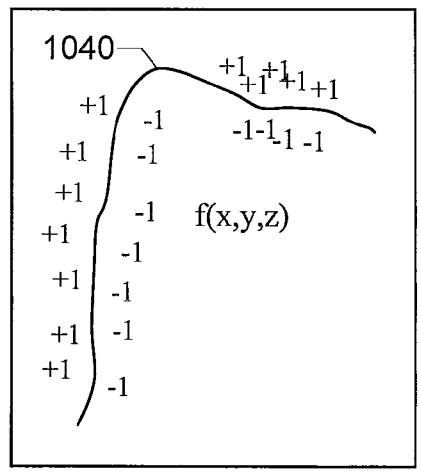

The process is illustrated in FIGS. 10b-d. In particular, FIG. 10b shows the local surface representations with their respective local surface normals. The generated off-surface points are labelled "+1" and "−1", respectively. FIG. 10c shows the generated modified point cloud with the function values f(x,y,z)=1 and f(x,y,z)=−1 assigned to the respective points. FIG. 10d shows the fitted function 1040.

Figure 11:
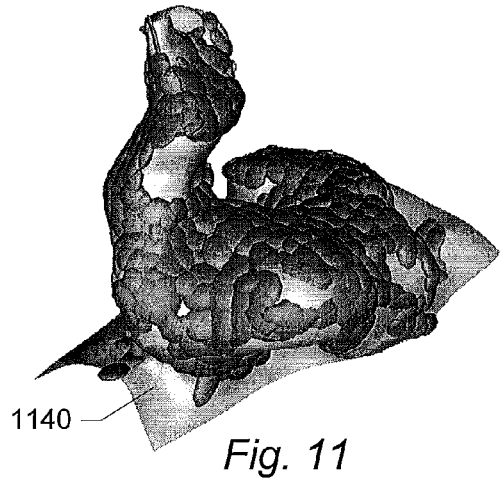
FIG. 11 shows an example of a reconstructed surface obtained from the local surface representations of FIG. 5.

FIG. 11 shows an example of the surface 1140 generated by FastRBF based on the density defined by the local surface representations of FIGS. 8 and 9. In FIG. 11, the reconstructed surface 1140 is shown together with the local surface representations on the basis of which the surface 1140 was generated.

The FastRBF surface reconstruction algorithm is excellent at extrapolation so it extends beyond the areas with good support by local surface representations. In order to provide feedback to the operator during the scanning process, it is desirable to determine where the generated surface ends and where there are "holes" in the surface. Therefore, the process determines which surface parts/patches have local support by a valid local surface representation. To this end, a "hole" may be defined as an area with no support by a local surface representation, but where the area is surrounded by areas with support by local surface representations.

Figure 12:
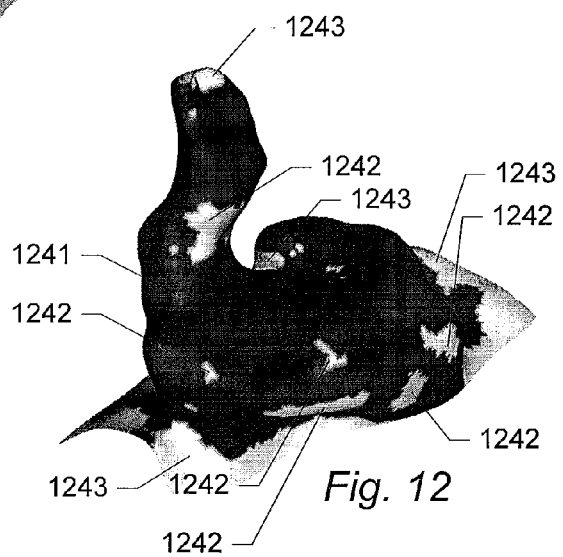
FIG. 12 illustrates a result of a labelling step where vertices without support by a local surface representation are shown light grey, while vertices with support of a local surface representation are shown dark grey.

Accordingly, in step S74 the process determines and marks all vertices of the reconstructed surface 1140 according to their distance to the closest local surface representation. Vertices having a distance larger than a predetermined threshold are labelled as having no support by a local surface representation. The result of this labelling step is illustrated in FIG. 12, where vertices above the threshold are shown light grey, while vertices with support by local surface representations are shown dark grey. Hence, there is good support in the dark surface regions 1241, while the light regions 1242 and 1243 are determined as being not or not sufficiently supported.

Figure 13:
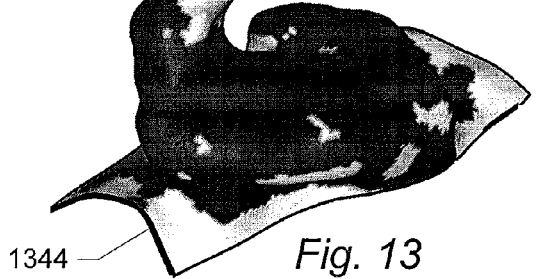
FIG. 13 shows a reconstructed surface where the edge of the surface is marked as a dark line.

In step S74, the process determines where there are holes in the surface and where there are surface boundaries with no support. To this end, the process may mark all triangles with edge vertices are. An edge vertex is a vertex that is only part of a single triangle, while non-edge vertices belong to two triangles. FIG. 13 shows the thus detected edge 1344. The detected boundary 1344 of the surface may then be used in a subsequent cropping algorithm. The process may use a flood fill algorithm to remove all triangles that are connected to a boundary and that have no support by a local surface representation. The result is illustrated in FIG. 14, where the holes are still shown as light areas 1242, but where the edge areas 1243 of FIG. 12 have been removed. Also the small holes have been removed if FIG. 12 and FIG. 14 are compared, as there is also a user defined threshold for the size (the area) of the holes. If the hole has an area less than this threshold it is simply ignored and considered as part of the reconstructed surface. For the ear canal a minimum hole area is 50 squaremillimetres.

In step S75, the biggest hole is determined using yet another graph algorithm. The process may thus indicate the biggest hole, e.g. by an arrow 1445 pointing to this hole, as shown in FIG. 14. The graph algorithm for determining the biggest hole may treat the surface mesh as a graph and then compute the connected clusters of triangles with no support. The clusters may be computed as described above in connection with the clusters of local surface representations. The area of a hole may be computed as the sum of triangle areas of the cluster.

Although some embodiments have been described and shown in detail, the invention is not restricted to them, but may also be embodied in other ways within the scope of the subject matter defined in the following claims. It will be appreciated that the method described herein may be implemented in connection with any suitable scanning technique that generates point cloud data.

For example, the apparatus and method described herein have mainly been described with reference to the obtaining of a data model of the ear canal. However, it will be appreciated that the apparatus and method described herein may also be applicable in connection with other cavities, such as other body cavities of the human or animal body, e.g. dental cavities, nasal cavities, the urethra, etc., as well as other surfaces including inner and outer surfaces of an object.

Embodiments of the method described herein can be implemented by means of hardware comprising several distinct elements, and/or at least in part by means of a suitably programmed microprocessor. In the apparatus claims enumerating several means, several of these means can be embodied by one and the same element, component or item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The invention claimed is:

1. A method for generating a digital representation of a surface of an object from point data indicative of coordinates of points on the surface, the method comprising:

receiving a point data item indicative of coordinates of a point in a first sub-volume of a plurality of sub-volumes of a volume to be scanned;

associating the point data item with the first sub-volume;

determining whether a count of point data items associated with the first sub-volume and not having been used as an input for computing a local surface representation exceeds a first predetermined threshold;

computing a local surface representation associated with the first sub-volume from received point data items associated with at least the first sub-volume based on an outcome of the determining whether the count of point data items exceeds the first predetermined threshold;

determining whether a count of computed local surface representations that have not yet been used as input for computing a surface representation of the surface of the object exceeds a second predetermined threshold; and computing the surface representation of the surface of the object from a set of computed local surface representations associated with respective sub-volumes based on an outcome of the determining whether the count of computed local surface representations exceeds the second predetermined threshold, the computing including clustering the set of the computed local surface representations based on one or more predetermined proximity conditions.

2. A method according to claim 1, wherein
computing a local surface representation associated with the first sub-volume comprises computing the local surface representation from received point data items associated with one of the first sub-volume and a predetermined proximity around the first sub-volume.

3. A method according to claim 1, wherein
computing the local surface representation comprises computing a measure of noise from the received point data items associated with at least the first sub-volume; and computing the local surface representation only if the measure of noise is smaller than a predetermined threshold.

4. A method according to claim 1, wherein
the local surface representation is an ellipsoid.

5. A method according to claim 1, wherein
computing the local surface representation comprises performing a Principal Component Analysis of the received point data items associated with at least the first sub-volume.

6. A method according to claim 1, wherein
the one or more predetermined proximity conditions is a condition on a distance between each member of a cluster and at least another member of the cluster.

7. A method according to claim 1, wherein computing the surface representation of the surface of the object comprises:
computing the surface representation of the surface of the object from the clustered local surface representations of clusters that include a number of cluster members exceeding a predetermined minimum number of cluster members.

8. A method according to claim 1, wherein computing the surface representation of the surface of the object comprises:
generating a plurality of points for each local surface representation; and
computing a surface reconstruction from the generated plurality of points.

9. A method according to claim 1, further comprising:
dividing the volume to be scanned into the plurality of sub-volumes; and
receiving the point data item indicative of coordinates of a point in the volume.

10. A method according to claim 1, further comprising:
displaying the computed surface representation of the surface of the object.

11. A method according to claim 1, further comprising:
obtaining a sequence of point data items indicative of coordinates of respective points on the surface.

12. A method according to claim 1, further comprising:
identifying one or more parts of the computed surface representation of the surface of the object having a distance from a closest one of the local surface representations, wherein the distance is larger than a predetermined minimum distance.

13. A method according to claim 12, further comprising:
displaying the computed surface representation of the surface of the object, and
displaying an indication of at least one of the identified one or more parts of the computed surface representation.

14. A method according to claim 1, wherein
the clustering the set of computed local surface representations generates one or more clusters of local surface representations based on one or more predetermined proximity conditions.

15. A method according to claim 14, wherein
the one or more predetermined proximity conditions is a condition on an angle between a local surface normal associated with a member of the cluster and a local surface normal associated with at least another member of the cluster.

16. An apparatus for obtaining geometrical data relating to a surface of an object, the apparatus comprising:
a measurement unit for obtaining point data items indicative of coordinates of respective points on the surface; and
a processing unit
configured to receive a point data item indicative of coordinates of a point in a first sub-volume of a plurality of sub-volumes of a volume to be scanned,
configured to associate the point data item with the first sub-volume,
configured to determine whether a count of point data items associated with the first sub-volume and not having been used as an input for computing a local surface representation exceeds a first predetermined threshold,
configured to compute a local surface representation associated with the first sub-volume from received point data items associated with at least the first sub-volume based on an outcome of the determining whether the count of point data items exceeds the first predetermined threshold,
configured to determine whether a count of computed local surface representations that have not yet been used as input for computing a surface representation of the surface of the object exceeds a second predetermined threshold,
configured to compute the surface representation of the surface of the object from a set of computed local surface representations associated with respective sub-volumes based on an outcome of the determining whether the count of computed local surface representations exceeds the second predetermined threshold, and
configured to cluster the set of the computed local surface representations based on one or more predetermined proximity conditions.

17. The apparatus according to claim 16, wherein
the measurement unit is configured to obtain geometrical data relating to an internal surface of a body cavity of a human or animal.

18. The apparatus according to claim 17, wherein
the body cavity is one of the ear canal, a dental cavity, a nasal cavity, and a urethra.

19. A computer readable tangible recording medium encoded with instructions, wherein the instructions, when executed on a data processing system cause the data processing system to perform a method, the method comprising:
receiving a point data item indicative of coordinates of a point in a first sub-volume of a plurality of sub-volumes of a volume to be scanned;
associating the point data item with the first sub-volume;
determining whether a count of point data items associated with the first sub-volume and not having been used as an input for computing a local surface representation exceeds a first predetermined threshold;

computing a local surface representation associated with the first sub-volume from received point data items associated with at least the first sub-volume based on an outcome of the determining whether the count of point data items exceeds the first predetermined threshold;

determining whether a count of computed local surface representations that have not yet been used as input for computing a surface representation of the surface of the object exceeds a second predetermined threshold; and computing the surface representation of the surface of the object from a set of computed local surface representations associated with respective sub-volumes based on an outcome of the determining whether the count of computed local surface representations exceeds the second predetermined threshold, the computing including clustering the set of the computed local surface representations based on one or more predetermined proximity conditions.

* * * * *